US006187906B1

(12) United States Patent
Gluckman et al.

(10) Patent No.: US 6,187,906 B1
(45) Date of Patent: Feb. 13, 2001

(54) METHODS TO IMPROVE NEURAL OUTCOME

(75) Inventors: Peter D. Gluckman; Christopher E. Williams; Jian Guan, all of Auckland (NZ)

(73) Assignee: Aukland Uniservices Limited, Aukland (NZ)

( * ) Notice: Under 35 U.S.C. 154(b), the term of this patent shall be extended for 0 days.

(21) Appl. No.: 09/332,868

(22) Filed: Jun. 15, 1999

Related U.S. Application Data

(63) Continuation-in-part of application No. 08/907,918, filed on Aug. 11, 1997.

(30) Foreign Application Priority Data

Jun. 15, 1998 (NZ) ............................................. 330684

(51) Int. Cl.[7] ................................................. C07K 5/083
(52) U.S. Cl. ............................................. 530/331; 514/18
(58) Field of Search .............................. 514/18; 530/331

(56) References Cited

U.S. PATENT DOCUMENTS 5,686,423 * 11/1997 Wang ...................................... 514/18

FOREIGN PATENT DOCUMENTS

| 52601/86 | * | 7/1986 | (AU) . |
| 0366638 | * | 5/1990 | (EP) . |
| 93/02695 | * | 2/1993 | (WO) . |
| 95/17204 | * | 6/1995 | (WO) . |

OTHER PUBLICATIONS

Guan, Neuroscience 89, 649, 1999.*
Saura, Neuroreport 10, 161, 1999.*
Alexi, Experimental Neurology 159, 84, 1999.*
Guan, *J. Cereb. Blood Flow Metab. 13*, pp. 609–616, 1993.*
Nilsson–Hakansson, *Neuro Report 4*, pp. 1111–1114, 1993.*
Sara, Molecular Biology and Physiology of Insulin and Insulin–Like Growth Factors New York, pp. 439–448, 1991.*
Sara, Biochem. Biophys. Res. Commun. 165, 766, 1989.*
Sara, Ann. N.Y. Acad. Sci. 692, 183, 1993.*

\* cited by examiner

*Primary Examiner*—Christopher S. F. Low
(74) *Attorney, Agent, or Firm*—Nixon & Vanderhye

(57) ABSTRACT

Disclosed herein is a method for protecting dopaminergic neurons of a mammal against death resulting from Parkinson's disease. The method comprises administering a neuroprotective amount of the tripeptide Gly-Pro-Glu.

11 Claims, 9 Drawing Sheets

METHODS TO IMPROVE NEURAL OUTCOME

This application is a continuation-in-part of application Ser. No. 08/907,918, filed Aug. 11, 1997.

TECHNICAL FIELD OF THE INVENTION

This invention relates to methods for the treatment or prevention of central nervous system (CNS) cell damage in mammals—also peripheral nervous system protection—and more particularly relates to a method of increasing the concentration of specified naturally occurring or introduced 2- or 3-peptides within the central nervous system to treat an injury or disease affecting or liable to affect dopaminergic neurons.

BACKGROUND OF THE INVENTION

The central nervous system is peculiar among mammalian organs in that differentiated neurones are practically incapable of regeneration. Permanent loss of function is a likely outcome of a sufficiently severe injury to the brain. It is particularly sad to meet children whose brains have been damaged by hypoxia during a difficult birth. There is therefore a need for means to protect cells of the central nervous system (also including the glial cells) from death after an injury.

After asphyxial, traumatic, toxic, infectious, degenerative, metabolic, ischaemic or hypoxia insults to the central nervous system (CNS) of man or other mammals a certain degree of damage in several different cell types may result. For example periventricular leucomalacia, a lesion which affects the periventricular oligodendrocytes is generally considered to be a consequence of hypoxic ischemic injury to the developing preterm brain (Bejar et al., Am. J. Obstet. Gynecol., 159:357–363 (1988); Sinha et al., Arch. Dis. Child., 65:1017–1020 (1990); Young et al., Ann. Neurol., 12:445–448 (1982)). Damage to the CNS by trauma, asphyxia, ischemia, toxins or infection is frequent and may cause sensory, motor or cognitive deficits. Glial cells which are non-neuronal cells in the CNS are necessary for normal CNS function. Infarcts are a principal component of some hypoxia ischemic induced damage and loss of glial cells is an essential component of infarction. There appears to be a kind of "delayed injury process" in which apparently "self-destructive" neural activity occurs some time after an injury; attempts to control this activity appear able to alleviate the effects of this delayed injury process.

Diseases of the CNS also may cause loss of specific population of cells. For example multiple sclerosis is associated with loss of myelin and oligodendrocytes, similarly Parkinson's disease is associated with loss of dopaminergic neurons. Some situations in which CNS injury or disease can lead to predominant loss of neurons and/or other cell types include: perinatal asphyxia associated with fetal distress such as following abruption, cord occlusion or associated with intrauterine growth retardation; perinatal asphyxia associated with failure of adequate resuscitation or respiration; severe CNS insults associated with near-miss drowning, near-miss cot death, carbon monoxide inhalation, ammonia or other gaseous intoxication, cardiac arrest, collapse, coma, meningitis, hypoglycaemia and status epilepticus; episodes of cerebral asphyxia associated with coronary bypass surgery; cerebral anoxia or ischemia associated with stroke, hypotensive episodes and hypertensive crises; and cerebral trauma.

There are many other instances in which CNS injury or disease can cause damage to cells of the CNS. It is desirable to treat the injury in these instances. Also, it is desirable to prevent or reduce the amount of CNS damage which may be suffered as a result of induced cerebral asphyxia in situations such as cardiac bypass surgery.

We have previously shown (in New Zealand Patent Application No. 239211—"IGF-1 to improve neural outcome", the contents of which are hereby incorporated by way of reference) that the growth factor called insulin-like growth factor 1 (IGF-1) has an unanticipated action, namely to prevent brain cells from dying after an asphyxial or ischemic brain insult (Gluckman et al Biochem Biophys Res Commun 182:593–599 1992). Because insulin also has a neuroprotective action (Voll et al Neurology 41:423–428 (1991)) and insulin and IGF-1 can both bind to the IGF-1 receptor, it was generally assumed that this brain rescue mode of action of IGF-1 was mediated via the IGF-1 receptor (Guan et al J. Cereb. Blood Flow Metab. 13:609–616 (1993)).

It is known that IGF-1 can be modified by proteolytic cleavage in nervous tissue to des 1-3N IGF-1, that is IGF-1 missing the 3 amino acids from the amino terminal of the molecule, and hence after cleavage there is also a 3 amino acid peptide gly-pro-glu which is the N terminal tripeptide. This tripeptide is also termed GPE. As des 1-3N IGF-1 also binds to the IGF-1 receptor and GPE does not, the GPE was thought to be of no significance to the neuronal rescue action of IGF-1.

Our previous work had shown that the brain increases its production of IGF-1 following brain injury by hypoxia-ischemia and that in addition it increases the synthesis of two specific binding proteins. IGF binding protein-2 (IGFBP-2) and IGF binding protein-3 (IGFBP-3) (Gluckman et al Biochem Biophys Res Commun 182:593–599 (1992) and Klemp et al Brain Res 18:55–61 (1992). These were hypothesised to attract the IGF-1 into the region of injury to reach concentrations necessary for neuronal rescue. For this reason IGF-1 was anticipated to be more potent given at a site distant from the injury than des 1-3 N IGF-1 which does not bind well to the binding proteins. This was indeed the case—1-3 N IGF-1 was not significantly active as a neuronal rescue agent at a dose equivalent to that at which IGF-1 shows neuronal rescue activity. Thus the prior art pointed to activity at the IGF-1 receptor as the mode of neuronal rescue achieved with IGF-1.

To date, there has been no enabling reference in the prior art to the manipulation of the cleaved tripeptide GPE itself to prevent or treat CNS injury or disease leading to CNS damage in vivo.

One disease which leads to CNS damage in vivo is Parkinson's disease. Parkinson's disease is the second most prevalent neurodegenerative disorder after Alzheimer's. It is a chronic and progressive motor system disorder and is distinguished by a tremor at rest, muscular rigidity, a slowness of movement initiation and movement execution and a mask-like appearance to the face.

The cause of this disease is unknown but the symptoms are a consequence of an 80% or greater loss of the dopaminergic neurons (which produce dopamine) in the pars compacta region of the substantia nigra.

OBJECT OF THE INVENTION

It is an object of the invention to provide a method for treating or preventing damage to dopaminergic neurons so that these neurons are protected from death resulting from Parkinson's Disease, or which will at least provide the public with a useful choice.

STATEMENT OF THE INVENTION

Accordingly, in a broad aspect the invention comprises a method for protecting dopaminergic neurons of a mammal against death resulting from Parkinson's Disease comprising the step of administering to said mammal a neuroprotective amount of a peptide selected from the tripeptide gly-pro-glu (GPE) and analogues thereof.

Preferably, the peptide administered in GPE. The GPE will usually be administered subsequent to onset of Parkinson's disease but prior to death of said dopaminergic neurons.

Conveniently, GPE is administered in the form of a pharmaceutical composition including a pharmaceutically acceptable carrier therefor.

GPE can be administered directly to where the dopaminergic neurons to be protected are located, such as by being preferably administered directly to the brain or cerebrospinal fluid by cerebro-ventricular injection, by injection into the cerebral parenchyma or through a surgically inserted shunt into the lateral cerebro ventricle of the brain.

In one form, GPE is administered in combination with artificial cerebrospinal fluid. GPE can also be administered systemically for transport to where the dopaminergic neurons to be protected are located, such as by being administered through an intravenous, oral, rectal, nasal, subcutaneous, inhalation, intraperitoneal or intramuscular route.

It will be usual for the dosage range of GPE administered to be from about 1 $\mu$g to about 100 mg of GPE per kg of body weight of the mammal.

Although the present invention is defined broadly above, it will be appreciated by those skilled in the art that it is not limited thereto but includes embodiments of which the description provides examples.

BRIEF DESCRIPTION OF THE DRAWINGS

A better understanding of the invention will be gained from reference to the foregoing examples and drawings wherein.

TECHNICAL DETAILS OF THE INVENTION

Figure 1:
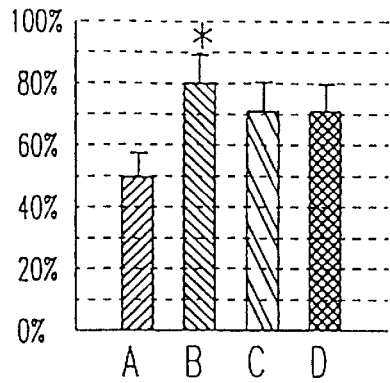
FIG. 1: shows the incidence of cortical infarction following treatment with vehicle along 50 $\mu$g of IGF-1 or the NMDA antagonist MK801 (1 mg) of IGF-1 plus MK801 2 hours after the hypoxia. Similar to previous studies the incidence of cortical infarction was lower in the IGF-1 treated group, whereas MK801 had a lesser effect.

We have explored the observations that insulin-like growth factor 1 (IGF-1) appears to be modified by proteolytic cleavage in nervous tissue to des 1-3N IGF-1, that is IGF-1 missing the 3 amino acids from the amino terminal of the molecule, and to a 3 amino acid peptide gly-pro-glu (GPE) which is the N terminal tripeptide. As des 1-3N IGF-1 also binds to the IGF-1 receptor and GPE does not, the GPE was thought to be of no significance to the neuronal rescue action of IGF-1. Surprisingly, GPE is effective.

Our previous work had shown that the brain increase its production of IGF-1 following brain injury by hypoxia-ischemia and that in addition it increases the synthesis of two specific binding proteins. IGF binding protein-2 (IGFBP-2) and IGF binding protein-3 (IGFBP-3) (Gluckman et al Biochem Biophys Res Commun 182:593–599 1992) and Klemp et al Brain Res 18:55–61 (1992). These were hypothesised to attract the IGF-1 into the region of injury to reach concentrations necessary for neuronal rescue. For this reason IGF-1 was anticipated to be more potent given at a site distant from the injury than des 1-3 N IGF-1 which does not bind well to the binding proteins. This was indeed the case—des 1-3 N IGF-1 was not significantly active as a neuronal rescue agent at a dose equivalent to that at which IGF-1 shows neuronal rescue activity. Thus the prior art pointed to activity at the IGF-1 receptor as the mode of neuronal rescue achieved with IGF-1.

To date, there has been no enabling reference in the prior art to the manipulation of GPE to prevent or treat CNS injury or disease leading to CNS damage in vivo.

Surprisingly, we have found that GPE itself appears to be the compound that underlies the phenomenon of neural rescue. (See for instance Example 3). This has led us to propose that treating a patient for neural injury or disease with IGF-1 is a less soundly based proposition, as tripeptide is easier to prepare, and as it is a more mobile and less immunologically challenging compound therefore it can be expected to be more effective.

Sara patent EP 0366638 A2 suggested that GPE could act as a neuromodulator to alter the activity of neuronal cells. Because it contains a glutamate and a glycine she suggested that it is likely to act at a NMDA class of receptor either as a partial agonist or antagonist. The classical NMDA receptor antagonist is MK801. We therefore compared the action of IGF-1 to MK801 given after injury and also looked for any additive effect.

Experiment 1 in our specification is a non-limiting example to show that in rats subject to hypoxic-ischemic injury the action of IGF-1 is not mimicked by or added to by use of NMDA receptor antagonist. This study shows that IGF-1 does not act by means of an action to modulate neural activity. In contrast, IGF-1, GPE and MK801 all have identical actions on gonadotropin release from hypothalamic tissue (Bourgignon et al Growth Regulation (in press)) suggesting that IGF-1 does act as a prohormone for GPE acting to modulate NMDA mediated neuronal activity in terms of hormone release and thus there was no a prior reason to anticipate that GPE would be a neuronal rescue agent. Thus there was no prior art to suggest that IGF-1 might act as a prohormone to form GPE which in turn stops neurons dying. Rather, the prior art suggests that IGF-1 acts via the IGF-1 receptors.

Experiment 2 is a non-limiting example in fetal sheep to show that IGF-1, which induced neuronal rescue is an ischemic model in fetal sheep, did not suppress cortical electroencephalographic activity whereas MK801 does so (Tan et al Ann Neurol 32:677–682 (1992)).

Experiment 3 is a non-limiting example which shows that despite the prior art suggesting that IGF-1 acts as a neural rescue agent via the IGF-1 receptor without modulating neuronal activity, GPE was as potent as a neuronal rescue agent as was IGF-1. The GPE was given shortly after the hypoxic ischemic injury but before degradation of DNA occurs in the regions which are destined in control animals to show neuronal death. The reduced degree of hippocampal neuronal loss and cortical infarction which is a reflection of less neuronal and less glial cell loss due to asphyxia. The mechanism by which GPE leads to prevention of cell death is not known but is clearly not by modulating neuronal activity.

Experiment 4 is a non-limiting example in 21-day old rats to show that GPE has a significant beneficial effect on neuronal outcome when given intraperitoneally, two hours after an insult comprising hypoxia.

Sara has shown GPE to modulate neuronal activity and, because agents such as NMDA which do, may have some role in treating neuronal injury, suggested but did not provide any evidence for its use as a treatment for neurological disease. However there is no prior art for our claims which are that GPE can be used to prevent neurological disease by preventing neurones and glia from dying. The type of clinical application to which our invention is directed is totally different from that of Sara.

More recent work by us tends to support the finding that the effects of GPE are most developed in the hippocampus itself; the CA1-2 regions. Thus our data relating to GPE and the like may be in the first instance most relevant to diseases primarily involving the hippocampus, and in the second instance to other populations of neurones once the modus operandi is better understood.

DESCRIPTION OF THE PREFERRED EMBODIMENTS

The invention relates to a method of manipulating neural damage. In a first aspect, the invention relates to a method of treating CNS damage after an injury to the CNS occurs. For example, the patient may have suffered perinatal asphyxia or asphyxia or cerebral ischemia associated with a stroke or other non-limiting examples of CNS injuries having been described earlier herein. In these instances, it is desirable to reduce or eliminate the symptoms of CNS damage.

CNS damage may for example be measured clinically by the degree of permanent neurological deficit cognitive function, and/or propensity to seizure disorders. (In our experiments we have used histological techniques).

It is proposed that the concentration of GPE and/or analogues thereof in the CNS and in the brain of the patient in particular should be increased in order to treat the CNS damage. Accordingly, GPE and/or analogues thereof can be administered directly to the patient. By the term "GPE" we refer in particular to gly pro glu or gly pro or pro glu. By analogues of GPE is meant compounds which exert a similar biological effect to GPE. These compounds can be derived from humans or other animals. GPE and analogues can be purified from natural sources or produced by synthetic techniques. Synthetic GPE can be obtained commercially.

Alternatively, compounds can be administered which, upon administration to the patient, increase the active concentration of GPE and/or naturally occurring analogues thereof in the CNS. By "active concentration" is meant the biological concentration of GPE and/or analogues in the CNS of the patient able to exert an effect on CNS damage. For example, elevating the active concentration of IGF-1 may enhance the formation of GPE.

GPE, analogues thereof and compounds which elevate the active concentrations thereof can be administered centrally or systemically. Desirably, the compositions are administered directly to the CNS of the patient. Accordingly, the compositions may be administered directly into the brain or cerebrospinal fluid by techniques including lateral ventricular through a burrhole, or anterior fontanelle, lumbar or cisternal puncture or the like.

If desired, a combination of the compounds can be administered. In addition they may be re-administered with other agents or growth factors, for example, transforming growth factor beta (TGF-$\beta$).

The foregoing experiments show that the expression of IGF-1 after a neural insult follows a specified time course and occurs in specified areas of the body. Accordingly, the compositions should be administered according to the pattern of CNS injury and the elapsed time subsequent to an injury so as to produce the most desirable results. The compositions may be administered directly to the region of the body where the greatest CNS injury has occurred.

The compositions may for example be administered about 0.5 to 100 hours after an injury and only one treatment may be necessary. Alternatively, repeated treatment may be given to the patient.

A suitable dosage range may for example be between about 0.1 to 1000 $\mu$g of GPE (and/or analogues or compounds that elevate the concentrations thereof) per 100 gm of body weight where the composition is administered centrally.

The treatment may be given before (as well as after) an injury—as for example before elective surgery. Examples of relevant elective procedures include neural surgery, in which retraction of lobes of the brain may lead to cerebral oedema, or heart operations, such as valve replacement, in which inevitable small emboli are said to lead to detectable impairment of brain function in some 75% of cases.

The invention also relates to a medicament for treating CNS injury. The medicament can comprise GPE and/or analogues thereof or a compound which elevates the concentration of GPE in the CNS such as IGF-1. The compounds are desirably provided in a pharmaceutically acceptable carrier or diluent such as those known in the art. GPE, analogues and compounds that elevate the concentration thereof can be manufactured by peptide synthesis techniques. Alternatively, the compounds can be isolated from natural sources.

A compound with little or no immunological effect may be administered over long periods, as long as other side effects prove to be unimportant. We propose that oral doses of a pharmaceutical compound promoting higher GPE levels in the brain (such as GPE itself) may be given over long periods to (for example) sufferers from chronic CNS disturbances such as Parkinson's disease, multiple sclerosis, Alzheimer's disease, and the like. In this instance the tripeptide nature of GPE should allow its entry into the circulation by direct absorbtion from the buccal mucosa from a lozenge placed under the tongue. We have shown that GPE is effective by intraperitoneal administration (in young rats) so it is at least not limited to injection into the CSF. The efficacy of GPE therapy in such diseases may be difficult to establish unless clinical trials are attempted.

The invention is supported by the following experimental data. In the following studies it was found that:

1) The neuronal rescue effect of IGF-1 is not mimicked or added to by use of an NMDA receptor antagonist.
2) Unlike an NMDA receptor antagonist neuronal rescue therapy with IGF-1 does not suppress seizure activity. Thus, the neuronal rescue effects of treatment with IGF-1 are not primarily mediated via the NMDA receptor.
3) Alterations in CNS levels of the n terminal tripeptide of IGF-1 called GPE can alter CNS damage resulting as a consequence of an injury to the CNS.
4) GPE is effective at maintaining the viability of dopaminergic neurons when threatened with death by the neurotoxin 6-hydroxy-dopamine, which makes GPE suitable for use in treating Parkinson's Disease.

The present invention is further illustrated by the following examples. These examples are offered by way of illustration only and are not intended to limit the invention in any manner. All patent and literature references cited throughout the specification are expressly incorporated. The studies described were approved by the Animal Ethical Committee of the University of Auckland.

Experiment 1

The objective of this study was to compare the effects of administering IGF-1 and the NMDA receptor antagonist MK801 after a CNS injury in order to clarify the site of action of IGF-1. The experiments involved treating the rats with vehicle, IGF-1, MK801 or IGF-1 plus MK801 2 hours after a CNS injury. These rats had an hypoxic-ischemic injury to one cerebral hemisphere induced in a standard manner. One carotid artery was ligated and the animal was subjected two hours later to a defined period of inhalational hypoxia. The degree, length of hypoxia, ambient temperature and humidity were defined to standardise the degree of damage. They were sacrificed five days later for histological analysis using stains (acid-fuchsin) specific for necrotic neurons. In such experimental cell death typically is restricted to the side of the side of arterial ligation and is primarily in the hippocampus, dentate gyrus and lateral cortex of the ligand hemisphere.

Adult Wistar rats (68 280–320 g) were prepared under 3% halothane/$O_2$ anaesthesia. The right side carotid artery was ligated. A guide cannula was placed on the dura 8.2 mm anterior from bregma and 1.4 mm from midline on the right. The rats were allowed to recover from anaesthesia for 1 hour and were then placed in an incubator with humidity 85±5% and temperature 34±0.5° C. for 1 hour before hypoxia. Oxygen concentration was reduced and maintained at 6±0.2 $O_2$ % hypoxia for 10 minutes. The rats were kept in the incubator for two hours after the hypoxia then treated either with IGF-1 (n=17), MK801 (n=17), MK801 plus IGF-1 (n=17) or vehicle (n=17)) were given via intra-ventricular (IVC) infusion. Simultaneously the rats were treated subcutaneously (IP) using 1 mg MK801/0.5 ml or saline alone. The intraventricular injections of 50 µg IGF-1 or vehicle alone were made into the right lateral ventricle at 1 µl/minute under 1.5%–2% halothane anaesthetic. Rats in each treatment group were infused simultaneously. The rats had free access to food during experiment and were euthanized at 120 hours after hypoxia with overdose of sodium pentobarbitol. Briefly, the brain was perfused in-situ with FAM (Formaldehyde, Acetic Acid, Methanol 1:1:8) then paraffin embedded. The sections were stained with Thionin and Acid Fuchsin. The presence of cortical infarction, defined as a region of tissue death or parenchymal pan-necrosis due to death of glia as well as neurons, was determined via light microscopy by an assessor who was blinded to the experimental groupings.

Results are illustrated in FIG. 1, showing the ratio between the R (ligated carotid) and L sides of the brain, wherein column A is vehicle, column B is 50 µg IGF-1, column C is 1 mg MK801, and column D is 50 µg IGF-1 with 1 mg MK801. (p(*)=0.031)

Similar to previous studies by ourselves the incidence of cortical infarction was lower following IGF-1 treatment (33%) compared to 65% in controls (Guan et al J Cereb Blood Flow metab 13:609–616 (1993)); whereas following MK801 treatment, the incidence was 50%. The combination of IGF-1 and MK801 was 41%. Thus in rats subject to hypoxic-ischemic injury the action of IGF-1 is not mimicked by or added to by use of NMDA receptor antagonist Experiment 2

The objective of this study was to compare the effects of treatment either with IGF-1 (see FIG. 2) and previously published work with the NMDA antagonist MK810 after an ischemic brain injury on postischemic seizures and neuronal losses in fetal sheep. (Tan et al Ann Neurol 32:677–682 (1992)).

The methods were those of an earlier study (Tan et al Ann Neurol 32:677–682 (1992)). Briefly, late gestation fetal sheep were chronically instrumented to record EEG, nuchal activity and blood pressure, and were then returned to the uterus. Cortical EEG activity nuchal activity and blood pressure were recorded throughout he experiment and the fetal brain subjected to 30 minutes of ischemia. Two hours later they were treated by an infusion of either 1 µg IGF-1 (n=6) or vehicle (artificial CSF) (n=6) into the lateral ventricle. Five days later the brains were fixed and assessed for neuronal loss as described previously (Tan et al Ann Neurol 32:677–682 (1992)).

Figure 2:
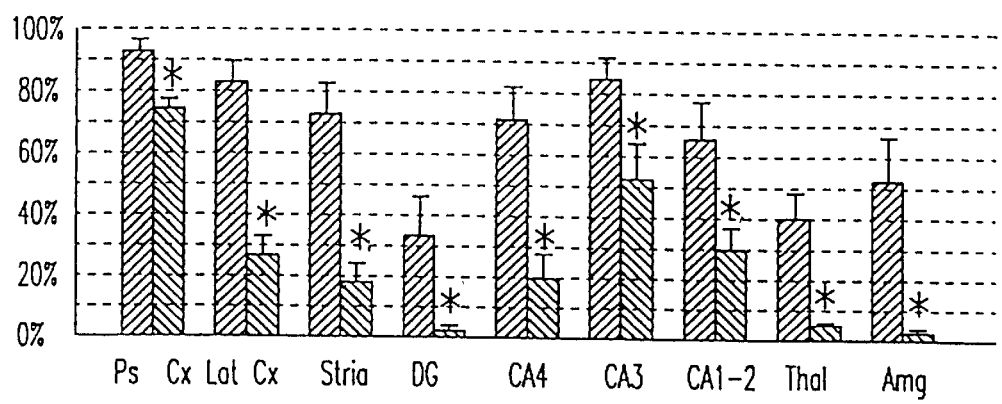
FIG. 2: shows an example of the effects of treatment with 1 $\mu$g IGF-1 2 hr after an ischemia in fetal sheep. The names under the horizontal axis are standard abbreviations for various portions of the brain. This dose was neuroprotective but, unlike MK801, did not suppress seizures.

FIG. 2 shows the neuronal loss scores for a number of regions of the brain (identified by abbreviations on the horizontal axis) as a percentage of the untreated side. In all cases the vehicle is the left-hand column and the effects of 1 μg of IGF-1 is on the right.

The results showed that, unlike the NMDA antagonist treated sheep, where electrical activity was markedly suppressed (Tan et al Ann Neurol 32:677–682 (1992)), IGF-1 rescued neurons (FIG. 2) but did not suppress the postischemic seizure activity in fetal sheep. This study also suggests that the neuroprotective effects of IGF-1 does not primarily occur via the NMDA receptor or altered electrical activity of the brain.

Experiment 3

The objective of this study was to compare the effects of treatment with GPE to that of vehicle given 2 hours after a hypoxic-ischemic brain injury.

The dose of 3 μm of GPE was chosen to be equivalent to that present in 50 μg of IGF-1 which has previously been shown to be neuroprotective (Guan et al J Cereb Blood Flow Metab. 13:609–616 (1993)). Unilateral hypoxic-ischemic injury was induced in adult 300±10 g) male Wistar rats. The rats underwent unilateral carotid ligation under light halothane anaesthesia. Following one hour recovery they were placed in an incubator at 34C at 85±5% humidity for one hour before injury. They were subjected to 10 min inhalational asphyxia (FiO2 6.0%) and maintained in the incubator for one hour after asphyxia. Two hours after the termination of the inhalation injury, a single stereotaxically controlled lateral cerebroventricular injection of either 3 μGPE (n=15) or phosphate buffered saline alone (n=15) was given. The animals were then maintained for 120 hrs, anaesthetized and the brains fixed in situ for histological assessment.

Figure 3:
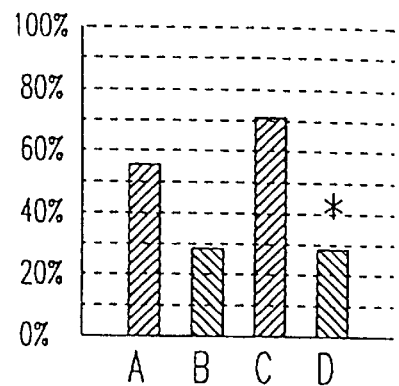
FIG. 3: shows the incidence of cortical infarction and hippocampal damage following treatment with 3 $\mu$g GPE or vehicle 2 hours after the hypoxia. [The incidence of hippocampal damage was reduced following treatment with 3 $\mu$g GPE. *p<0.05]

Surviving and dead neurons were discriminated with the use of a thionin/acid fuchsin staining technique [C. Williams, A. Gunn, C. Mallard, P. Gluckman *Ped Res.* (1990). A. Brown, J. Brierley, J. Neurol Sci, 16:59–84 (1971)]. The results are shown in FIG. 3; using a scoring technique. It is evident that there was neuronal damage even on the unligated side, yet GPE therapy reduced the incidence of hippocampal damage in the ligated hemisphere compared to the vehicle treated controls (p<0.05 by Fisher's exact test). Similar to our previous study with IGF-1 the incidence of cortical infarction was lower following GPE treatment at 27% compared to the control/vehicle treated rats at 53% (Guan et al J Cereb Blood Flow Metab. 13:609–616 (1993)).

FIG. 3 shows the incidence of cortical infarction (columns A and B) and hippocampal damage (columns C and D) following treatment with vehicle (columns A and C) or 3 μg GPE (columns B and D) two hours after the hypoxia. (The incidence of hippocampal damage was reduced following treatment with 3 μg GPE. The asterisk indicates a probability of under <0.05.

Figure 4:
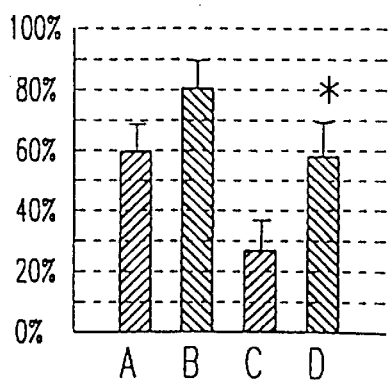
FIG. 4: shows results from the same experiment; wherein the two columns on the left shown the area (hence volume, from stereology) of viable cortical tissue remaining after treatment, as a ratio between the right side of the brain and the left (injured) side, while the two columns labelled CA-1 show the proportion of live neurons remaining (comparing right and left sides) after the insult.

FIG. 4 shows a later, more critical assessment of the same experiment. For this figure the columns A and B indicate the proportional loss of area (which can be extrapolated to indicate volume using the well-known principles of stereology) between the left and rights sides of the cortex of the brain, for either a control vehicle or 3 μG of GPE. Volumes were measured using computer-aided image analysis techniques. Columns C and D relate to the hippocampus and indicate the proportion of live neurones remaining after the experiment; again comparing right and left side counts. The asterisk indicates a probability of 0.04. Neurones were counted after staining, with the aid of a microscope. The administration of GPE has resulted in a significant reduction in the number of damaged cells. Thus a single central injection of GPE following an asphyxial injury in the adult rat was associated with a marked improvement in outcome as assessed histologically.

A histological experiment to locate GPE binding sites within the rat brain employed quantitative receptor autoradiography to locate [3H]-GPE binding in coronal sections of the brain as previously described in Dragunow et al (1988, Brain Research 462, 252–257). Fresh frozen brain sections were cut on a cryostat and stored at −80 deg C. until use. Sections were then thawed and pre-incubated with 50 mM Tris HCl (pH 7.4) for 10 minutes at room temperature (250 μl per section). Sections were then dried and 250 μl per section of $5\times10^5$ counts/min$^{-1}$ of [3H]-GPE also made up in Tris HCl buffer (50 mM, pH 7.4) was added for 1 hour at room temperature. Sections were then washed two times for one minute each in ice-cold Tris-HCl followed by one rinse for 1 minute in ice-cold distilled water. Sections were then dried overnight at 4 deg C. and apposed to [3H] sensitive film for 2 weeks, and then developed to produce autoradiograms.

Figure 6:
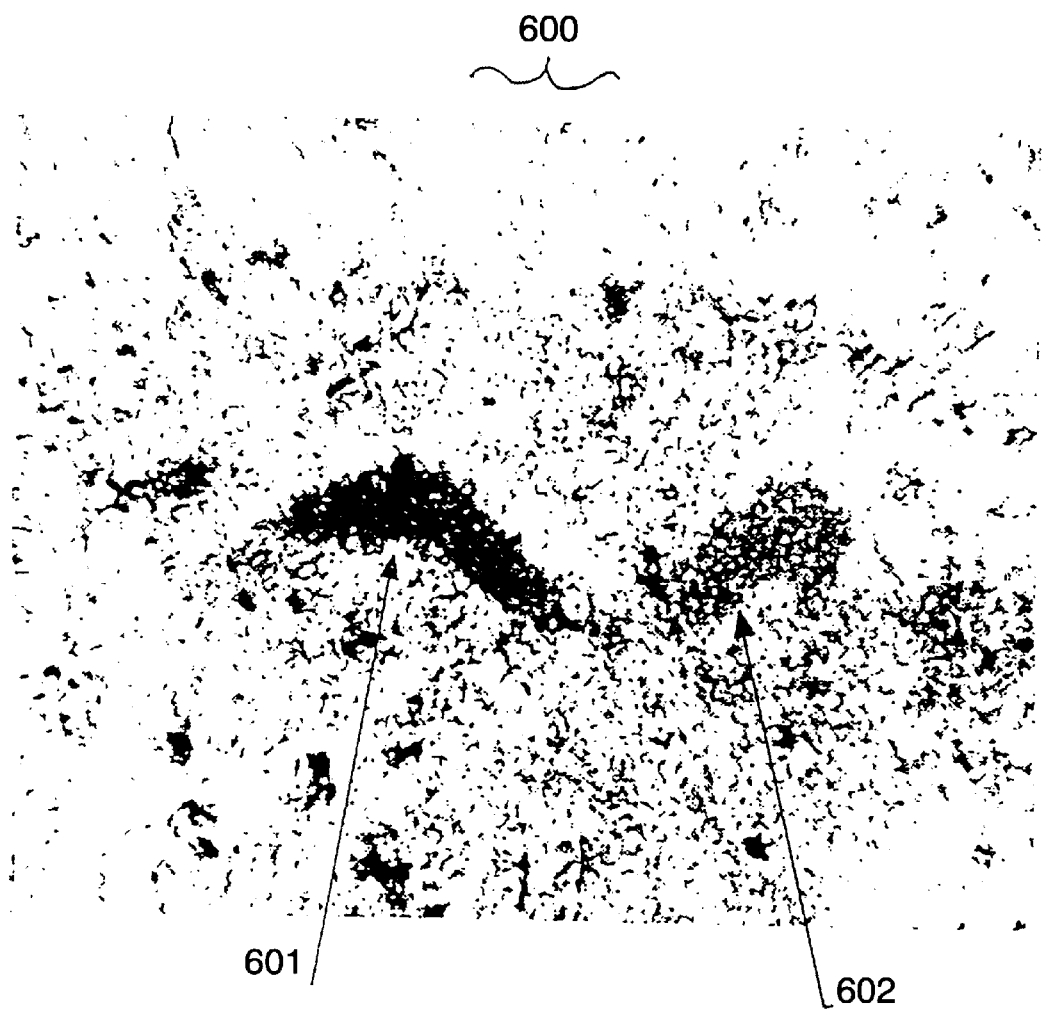
FIG. 6: is a photomicrograph which shows binding of GPE in an injured side of the hippocampus.

Results as illustrated in FIG. 6 show that the left hippocampus has bound the radioactive material while the corresponding side on the right shows little reaction. The neurons on this side were absent due to a pre-existing injury. This radioautograph illustrates a particular binding site for GPE and tends to support our belief that GPE provides particular benefit at this important nucleus.

Rationale for Experiments 4–7

Tyrosine hydroxylase (TH) is a rate limiting enzyme for dopamine production. It is produced by dopamine neurons as part of the dopamine production process. An upregulation of TH expression is therefore representative of an increase in dopamine production, and or viability of the population of dopamine neurons which express TH.

Experiment 4

This experiment was blind with respect to the treatment (with GPE or the vehicle) and with respect to the counting of neurons expressing TH (between sections from animals treated with GPE or vehicle).

The objective of this experiment was to determine the effects of administering GPE on the expression of tyrosine hydroxylase (TH) in the presence or absence of CNS injury. The experiment involved treating the rats with a control vehicle of GPE 2 hours after a chemically induced lesion in the substantia nigra region of the brain. Specifically, 9 pairs of adult male Wistar rats (280–320 g) were prepared under 3% halothane/$O_2$ anaesthesia. The oxygen free radical producing neurotoxin 6-hydroxydopamine (6-OHDA) which produces degeneration of dopamine neurones (8 μg/2 μl) was injected into the median forebrain bundle using a 30 gauge needle (coordinates: anterior-posterior +4.7 mm, right +1.6 mm, vertical −8.5 mm). A guide cannula was placed on the dura 7.5 mm anterior from stereotaxic zero and 1.5 mm from the midline on the right. The rats were left to recover at room temperature. 2 hours after the administration of 6-OHDA the rats were treated, via the guide cannula, with 3 μg GPE or vehicle alone (15 μl injected with a pump rate of 2 μl/minute, 0.1M acetate buffer [pH6], diluted 10 times in 0.1 bovine serum albumin in 0.1M phosphate buffered saline [PBS][pH7.3].

The rats were sacrificed using pentobarbital 14 days after 6-OHDA induced injury. Brains were perfused with normal saline and 4% paraformaldehyde and fixed in perfusion fixative overnight. The brains were paraffin embedded using a standard processing schedule. Sections (8 μm) were cut through the substantia nigra using a microtome. Immunoreactivity for TH was established with sections mounted on chrome alum coated slides. Briefly, the sections were dewaxed, rehydrated and washed in 0.1M PBS. The sections were pre-treated with 1% $H_2O_2$ in 50% methanol for 20 minutes and then washed in 0.1M PBS (5 minutes×3). The antibodies were diluted in 1% goat serum. The sections were then incubated with rabbit (Rb) anti-TH (1:500) antibodies (the primary antibodies) for 2 days. The sections were washed using 0.1M PBS (5 minutes×3) and then incubated with goat anti-rabbit biotinylated secondary antibodies (1:200) at room temperature overnight. The sections were washed in 0.1M PBS (5 minutes×3) and then incubated in (ExtrAvidin TM Sigma 1:200) for 3 hours and followed by $H_2O_2$ (0.01%) in 3,3-diaminobenzidine tetrahydrochloride (DAB, 0.05%) reaction. The sections were then dehydrated and coverslipped.

The neurons in the pars compacta region of the substantia nigra at 3 levels in both hemispheres which showed specific immunoreactivities corresponding to TH were counted using a light microscope. The total counts of neurons were compared between the GPE and the vehicle treated group. Data were analysed with paired t-test and presented as mean ±sem. The results are presented in FIG. 7.

Figure 7:
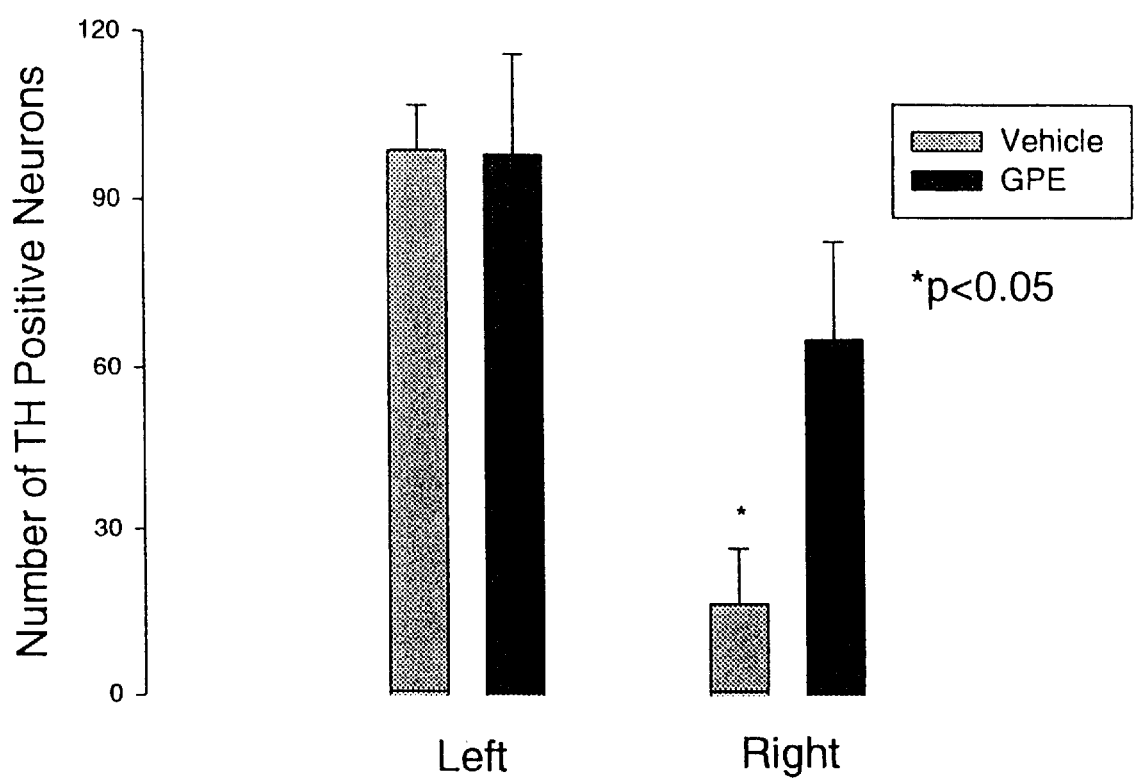
FIG. 7: shows the number of TH immunopositive neurons following treatment with a control vehicle or with GPE two hours after administration of a neuro-toxin.

FIG. 7 shows that the number of TH immunopositive dopamine neurons increased with GPE on the lesioned (right) side of the brain. This indicates that the administration of GPE is effective in upregulating TH expression.

Experiment 5

Experiment 5 was performed using a second set of rats (9 pairs) using the same experimental parameters except that only the immunopositive neurons at 2 levels of the substantia nigra were counted.

Figure 8:
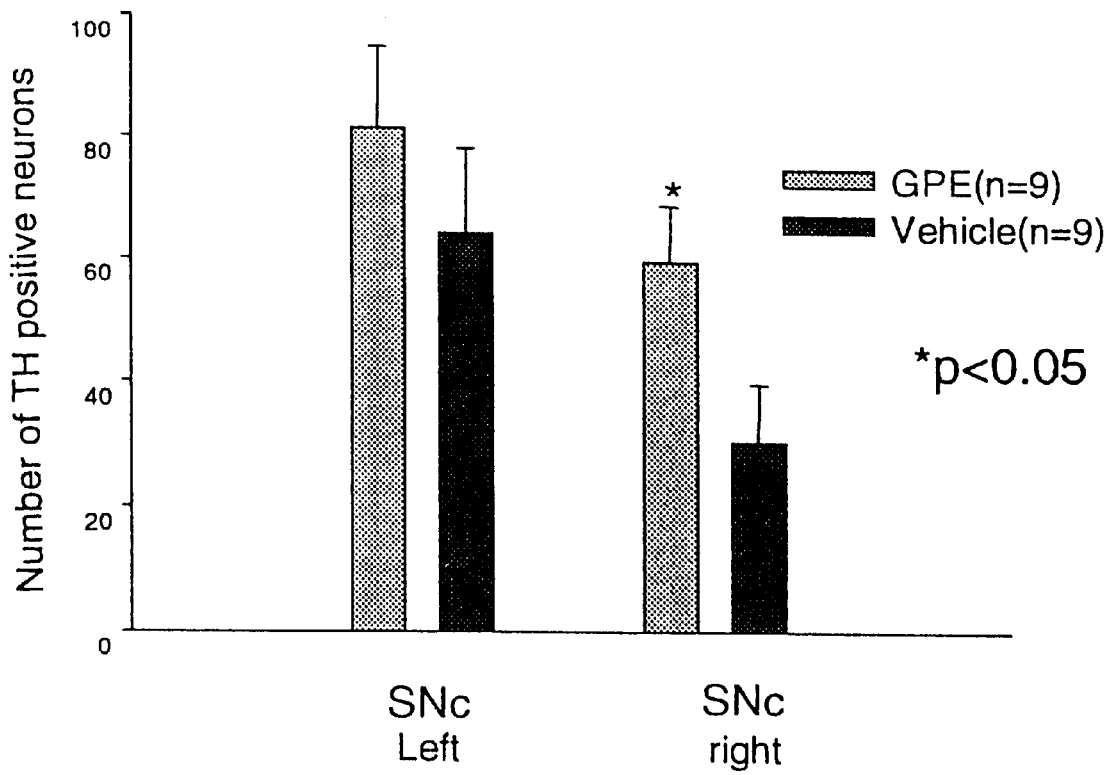
FIG. 8: shows the number of TH immunopositive neurons following treatment with a control vehicle or with GPE two hours after administration of a neuro-toxin.

The results are shown in FIG. 8, and again demonstrated upregulation of TH expression.

Discussion

The above experiments (4 and 5) show the effect of GPE administration on TH expression in the pars compacta region of the substantia nigra (SNc). GPE provided protection for the dopaminergic neurons against the neurotoxin 6-OHDA.

Experiment 6

Ethics approval

These experiments were approved by the University of Auckland Animal Ethics Committee and all efforts were made to minimise the suffering incurred and the numbers of animals used.

Experimental design and animal preparation

A paired experimental design was used and the experimenter was blinded to the treatment groups. Eighteen male Wistar rats (50–60 days old, 280–310 g) were used for this study. 6-hydroxy dopamine (6-OHDA) was prepared as 8 μg in a base of 2 μl 0.9% saline containing 1% ascorbic acid. It was administered into the right medial forebrain bundle (MFB) using coordinates of AP +4.7 mm, R 1.6 mm, V −8 mm under anaesthesia of 3% halothane, 6-OHDA was injected into the right MFB using a Hamilton syringe (100 μl with a 30G needle) controlled by a microdialysis infusion pump at an infusion rate of 0.2 μl/minute. The infusion needle was then slowly withdrawn 5 minutes after infusion. The surgery procedures for the intracerebroventricular administration have been described by Guan et al (1993), *Journal of Cerebral Blood Flow and Metab*, 13, 609–616. Briefly, a guide cannula (21G, 6 mm) was fixed on the top of the dura with coordinates of AP +7.5 mm, R 1.5 mm immediately after the injection of 6-OHDA. Either GPE (3 μg/15 μl) or its vehicle were infused into the right lateral ventricle 2 hours later at an infusion rate of 2 μl/minute (Guan et al (1993)). Rats were then housed in a holding room with food and water ad libitum for the next 2 weeks.

The rats were then deeply anaesthetized with an overdose of pentobarbital and transcardially perfused with normal saline followed by 10% buffered formalin. The brains were removed from the skull and kept in the same fixative for the next 48 hours. A standard paraffin tissue preparation was used to process the tissue so that it could be used for immunohistochemistry. Coronal sections (8 μm) were cut using a microtome, and the sections were mounted on chrome alum coated microscopy slides and air-dried. Substantia nigra sections used for immunohistochemical staining were deparaffinized, rehydrated and washed in PBS (0.1M). The sections were then pretreated with 1% $H_2O_2$ for 20 minutes, washed with 0.1M PBS (3×5 minutes) and incubated with rabbit polyclonal antisera raised against tyrosine hydroxylase (Protos Biotech, USA) diluted 1:500 with 1% goat serum for 48 hours at 4° C. The sections were washed in PBS (3×5 minutes) and incubated with donkey anti-rabbit biotinylated secondary antibody (1:200, Amersham, Life Science) overnight at room temperature. The sections were washed, incubated in streptavidin-biotinylated horseradish peroxidase (1:200, Amersham, Life Science) for 3 hours, washed again in PBS and then reacted in 0.05% 3,3-diaminobenzidine tetrahydrochloride (DAB) and 0.01% $H_2O_2$ to produce a brown reaction product. The sections were dehydrated in a graded alcohol series, cleared in xylene and coverslipped with mounting medium.

Tissue evaluation and statistics

The number of TH positive neurons on both sides of the SNc were counted using light microscopic examination (20×magnification) at three representative levels (AP +4.2, +3.8 mm and +4.3 mm) (Paxinos, et al (1982) New York: Academic Press).

The average density from the background was also measured. The analyst was blinded to the treatment and control groups. The difference in average density between the background and TH immunostaining was calculated and used for data analysis. Right/left (R/L) ratios of both the number of TH immunopositive neurons and the average density of TH immunostaining from each level was compared between the two treatment groups using one way ANOVA. Data are presented as mean ±SEM.

Results

Figure 9:
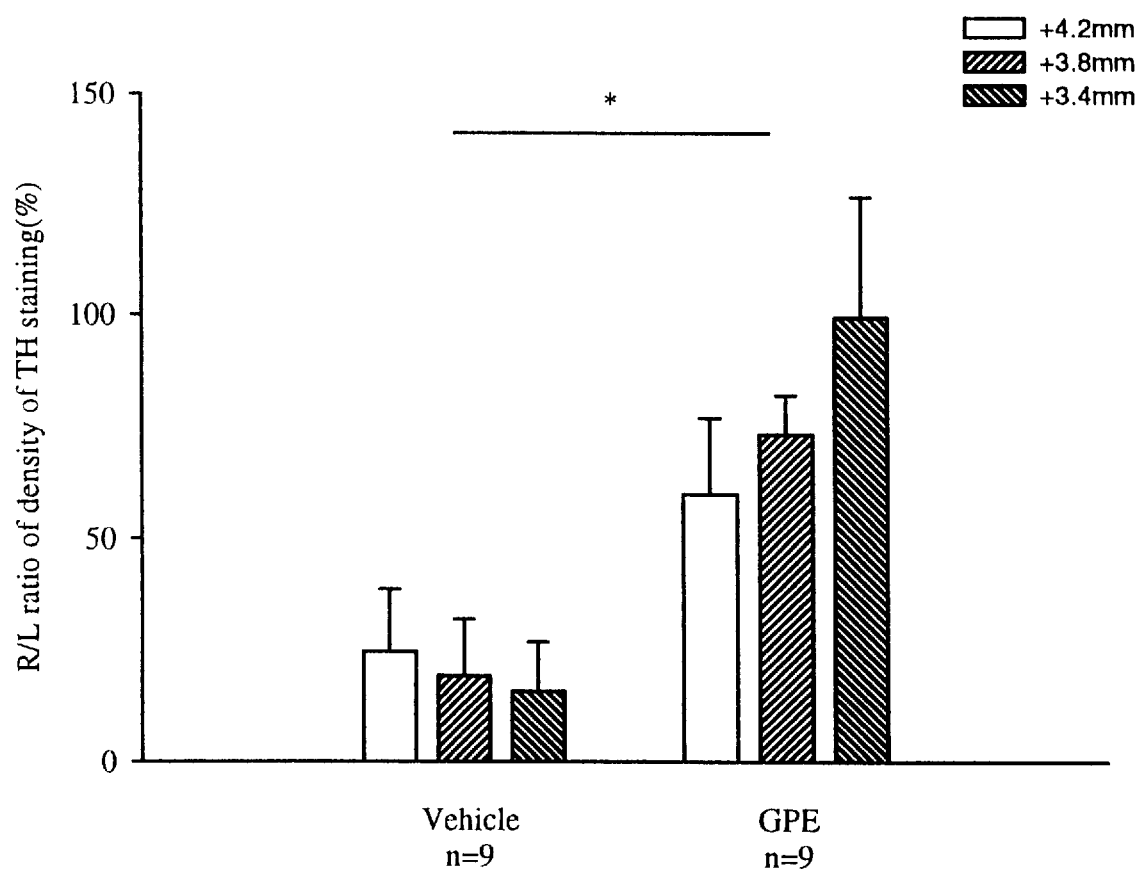
FIG. 9: shows the density of TH immunopositive staining following treatment with a control vehicle or with GPE two hours after administration of a neuro-toxin.

FIG. 9 shows that TH immunoreactivity was restored with GPE on the lesioned (right) side of the brain. This effect was more pronounced in caudal levels (16±11.2 to 99.6±27%) compared with the rostral level (FIG. 9). This indicates that the administration of GPE is effective and selective in upregulating TH expression, and in maintaining the viability of the dopaminergic neurons which express the enzyme.

Figure 10:
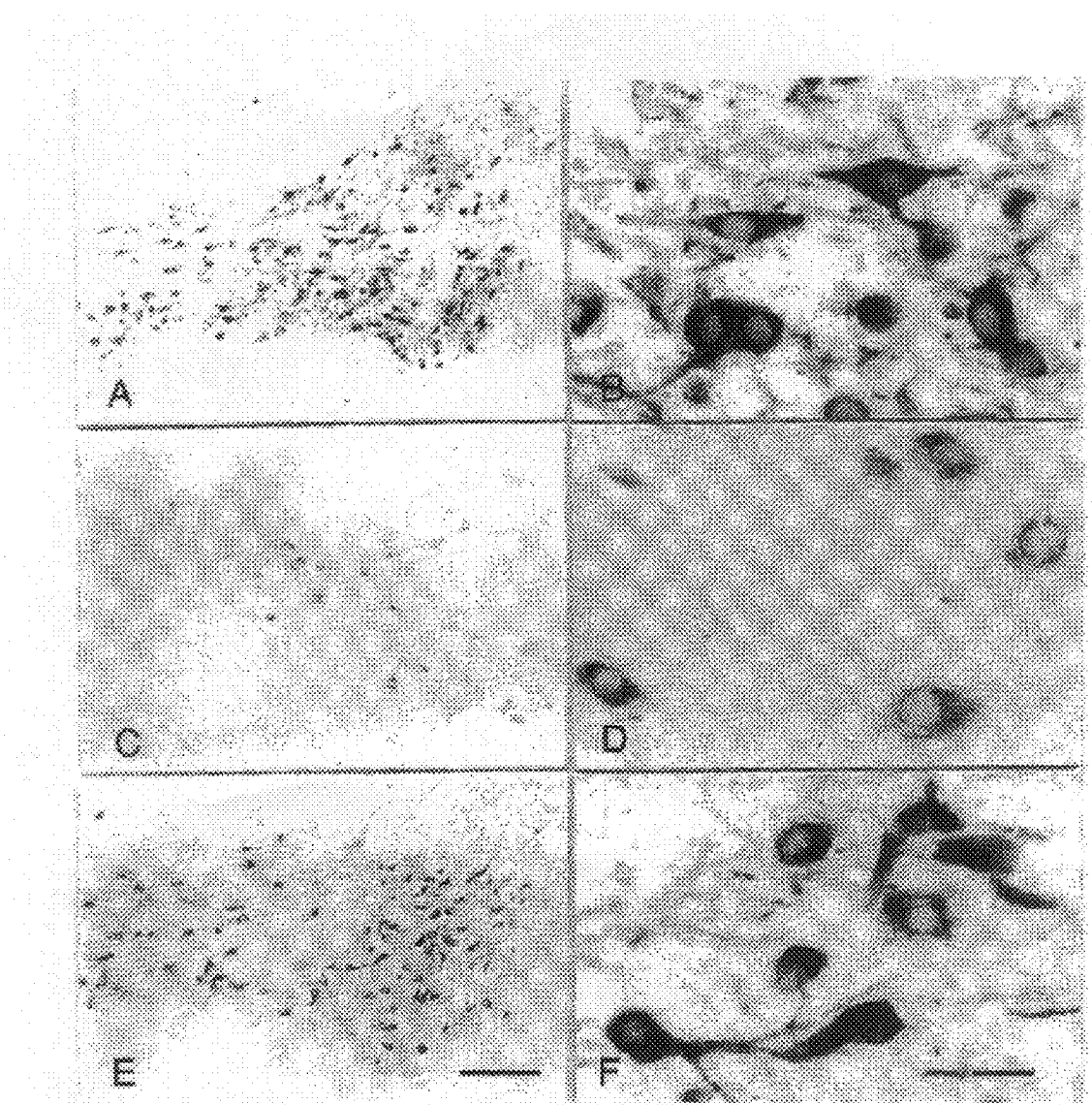
FIGS. 10A–10F show photomicrographs of immunohistochemical labelling of the SNc with an antibody against TH. A, C and E are at 10× magnification and B, D and F are at 40× magnification. A and B are photomicrographs of control sections of the right side of the BNc. C and D are photomicrographs from ipsilateral SNc where the vehicle was administered intraventricularly 2 hours after lesioning with 6-OHDA. Note the major decrease in TH immunoreactivity in C and the decreased immunoreactivity in the cell body and processes in D. E and F are photomicrographs of the ipsilateral SNc where GPE was administered intraventricularly 2 hours after lesioning with 6-OHDA. Scale bars A, C, E=0.5 $\mu$m, B, D, F=20 $\mu$m.

GPE treatment restored the density of immunostaining in both the cytoplasm and processes of neurons (FIG. 10).

Figure 11:
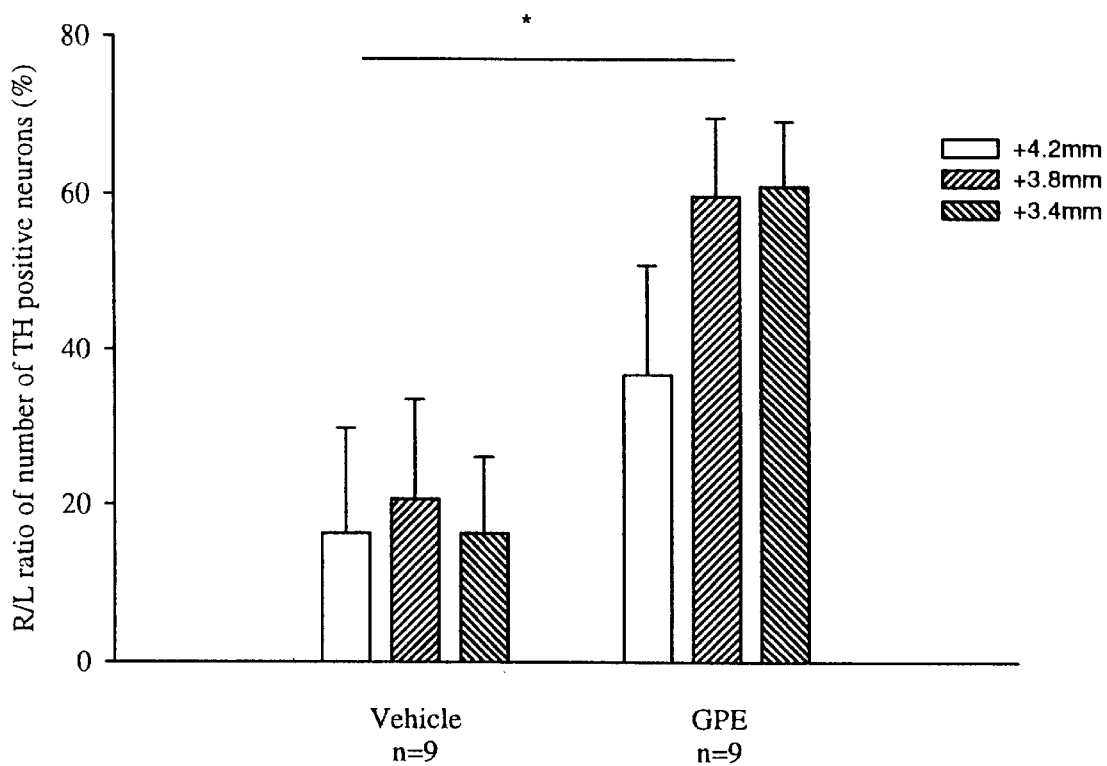
FIG. 11: shows the neuronal rescue effect of GPE on TH immunopositive neurons following 6-OHDA lesion in the SNc.

FIG. 11 shows that treatment with a single dose of GPE (3 μg) significantly improved the percentage of neuronal survival in the ipsilateral SNc compared to the vehicle treated group (17.7±6.6–52.2±7.0%, p<0.001). The treatment effect was most pronounced in caudal levels where over 60.9±13.0% of the neurons remained compared with 16.3±11.5% in vehicle treated rats.

Discussion/Conclusions

The above experiment shows the effect of GPE administration on TH expression in the SNc. GPE was particularly effective in upregulating TH expression in the most caudal region of SNc analysed. GPE upregulated TH expression in the cytoplasm of both the neuronal cell body and neuronal processes. GPE prevented the loss of TH immunopositive neurons in the SNc compared to the control group. GPE provided protection for the dopaminergic neurons against the neurotoxin 6-OHDA.

Experiment 7

Ethics approval

These experiments were approved by the University of Auckland Animal Ethics Committee and all efforts were made to minimise the suffering incurred and the numbers of animals used.

Medial forebrain bundle transection and cannulation

Adult male Wistar rats (200–220 g) were anaesthetized with 75 mg/kg Nembutal and positioned in a stereotaxic apparatus. Unilateral transection of the medial forebrain bundle which contains the ascending nigral dopaminergic projection fibers was made 1.3 mm rostral to the rostral tip of the substantia nigra using a retractable wire knife (David Kopf Instruments, Tujunga, Calif.). The knife was lowered into the brain using the following coordinates from the atlas of Paxinos and Watson (1996), Sydney: Academic Press: 3.3 mm posterior to Bregma, 2.4 mm lateral from midline, and 8.5 mm ventral from skull, the blade was extended 2.0 mm toward midline, raised 2.5 mm dorsally, retracted and extended again, and then returned 2.5 mm ventrally. The wire blade was retracted and the knife withdrawn. Next, a 22-gauge metal guide cannula was permanently fixed into place supranigrally at 5.0 mm posterior to Bregma, 2.0 mm lateral to midline, and 6.8 mm ventral to skull. A second set of intact unlesioned rats were cannulated supranigrally at the same coordinates.

Neurotrophic factor infusion

Animals received daily supranigral injections of trophic factors via a Hamilton syringe attached to a 28-gauge cannula 1 µl of either GPE (0.3 µg/µl), or 1 µg of the control vehicle PBS with 0.1% bovine serum albumin (BSA) beginning immediately after lesioning and extending for two weeks post-lesioning. GPE was diluted in phosphate buffered saline (PBS) containing 0.1% BSA (pH 7.4).

Immunocytochemistry

After two weeks of treatment, animals were perfused under deep anaesthesia with PBS (pH 7.4) followed by 4% paraformaldehyde in phosphate buffer (pH 7.4). Brains were post-fixed for 24 hours at 4° C. in the same fixative then transferred sequentially to 10% and 30% sucrose in PB for 2–5 days until sunken. Floating 30 µm coronal nigral sections were stained by avidin-biotin-peroxidase immunocytochemistry. Rabbit anti-rat tyrosine hydroxylase (TH) polyclonal antibody (TE 101, Eugene Tech International, New Jersey, USA) was diluted 1:100 in PBS containing 0.2% Triton X-100, 3% goat serum, and 0.02% sodium azide. Sections were first incubated for 1 hour at room temperature in primary antibody vehicle. Incubation with the primary antibody was for 3–4 days at 4° C,. Biotinylated anti-rabbit IgG (Vector Laboratories) secondary antibody was diluted at 4 µl/ml in PBS containing 0.1% Triton X-100 and normal rabbit serum. Sections were incubated for 2 hours at room temperature, followed by an avidin-biotin-peroxidase cocktail (Vector Laboratories) incubation for 1 hour at room temperature. Peroxidase was visualized with 1 mg/ml 3,3'-diaminobenzidine in 0.03% $H_2O_2$ for 5 minutes. Controls were conducted by replacing the primary antibody with pre-immune IgG or by omitting the primary and/or secondary antibody from the procedure. Sections were mounted on gelatin-coated slides, dehydrated in serial ethanol, cleared in xylene and coverslipped with mounting media.

Quantification of cell number

Immunopositive cells were counted in the central substantia nigra. Counts were made ventral and lateral to the lemniscus medialis, including both the pars compacta and pars reticulata, but excluding the ventral tegmental area in the ventromedial midbrain and the retrorubral field in the caudolateral midbrain. A cell was counted if it had an intact cell body and soma membrane. Counts were taken on both the contralateral and ipsilateral sides from 2–3 animals per treatment. The number of cells was represented by the mean number of immunopositive cells within the described field on each side of the brain. To reveal percent survival, percent changes were calculated by dividing the ipsilateral value by contralateral value.

Results

Figure 12:
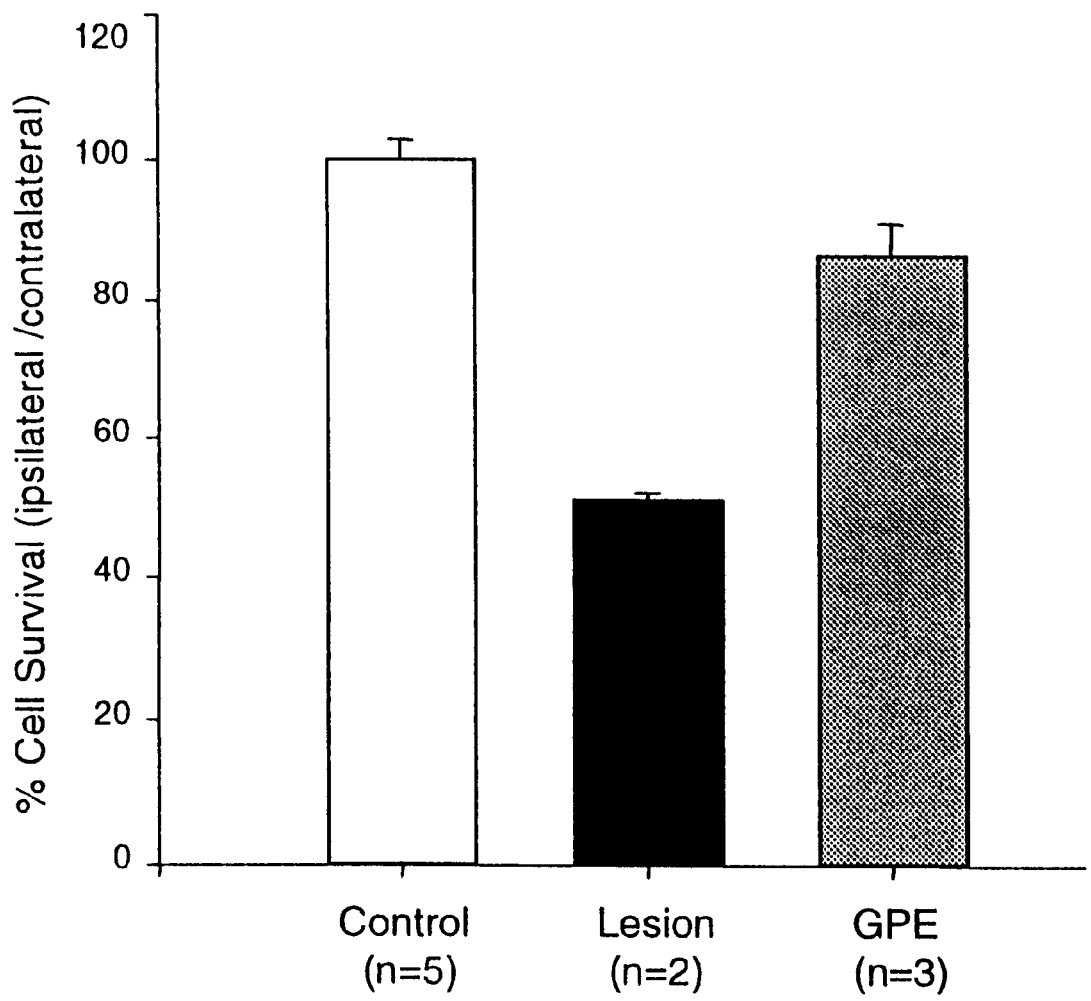
FIG. 12: shows cell counts expressed as percent cell survival of substantia nigra neurons after mechanical lesioning and treatment with GPE.

The percent cell survival of TH immunopositive neurons increased with GPE treatment on the lesioned side of the brain (FIG. 12). This indicates GPE is effective in upregulating TH expression, and in maintaining the viability of the dopaminergic neurons which express the enzyme.

Experiment 8

Materials and Methods

Embryonic mesencephalic cultures

Wistar rat ventral mesencephali from E15 (E1=plug) fetuses were dissected, pooled, and gently dissociate by repeated trituration in 3 ml of sterile modified Krebs-Ringer medium (Gibco, Life Technologies Ltd., NZ) supplemented per liter with 50,000 IU penicillin, 50 mg streptomycin, 1.26 g $NaHCO_3$, and 2.2 g glucose. 2 ml of media was added and the suspension allowed to stand for 7 minutes, after which the supernatant was centrifuged for 7 minutes at 350 xg. The pellet was resuspended in serum-containing media: MEM media with 50,000 IU penicillin, 50 mg streptomycin, 1.26 g $NaHCO_3$ and 5% fetal calf serum (Gibco). Cells were seeded at $2.5$–$4.0 \times 10^5$ trypan-excluding viable cells/cm² in sterile 24 well plates precoated for two hours with 5 µg/ml poly-L lysine in $H_2O$. Cultures were allowed to recover for 24 h at 37° C. in a humidified 95% air: 5% $CO_2$ incubator.

Medium was replaced with fresh serum containing medium supplemented with GPE (Bachem, final concentration 0.01, 0.1 1, 10 or 100 µM GPE) or vehicle (0.01% BSA in 0.1M PBS) and the cultures incubated for 30 minutes before the addition of 6-Hydroxydopamine (6-OHDA, Sigma, Missouri, USA, final concentration 4 µM) or vehicle ($H_2O$). The cultures were incubated for 18 h at 37° C. in a humidified 95% air: 5% $CO_2$ incubator. Medium was replaced with fresh serum containing medium supplemented with 0.01, 0.1, 1, 10 or 100 µM GPE or vehicle. Cultures were incubated for a further 4 days. The medium was replaced on the first day with fresh medium supplemented with 0.01, 0.1, 1, 10 or 100 µM GPE or vehicle and assayed for dopamine uptake.

Dopamine Uptake Assay

Cultures were assayed for dopamine uptake using a modified procedure of Prochiantz et al., 1981 (Nature, Vol. 293, No., 5833). Cultures were washed once with a pre-warmed incubation solution of PBS containing 5 mM glucose, 0.5 mM ascorbic acid, and 0.1 mM pargyline and pre-incubated for 5 minutes at 37° C. [$^3$H]Dopamine (21Ci/mmol, NEN) was added to give a final concentration of 50 nM. Cultures were incubated for 15 min at 37° C. and blanks were incubated at 0° C. Uptake was halted by rinsing once with PBS at 0° C. Cells were lysed with 250 μl of 1% Triton X-100 and 50 μl 60% perchloric acid for 15 minutes. Well contents were then transferred to scintillation vials. The wells were then rinsed with 250 μl 1% Triton X-100 and the contents added to the appropriate scintillation vial containing 4 ml of Ready safe scintillation fluid (Beckman, Palo Alto, Calif.). Counts were performed for 5 min in a LKB Wallac 1219 liquid scintillation counter. Blank samples yielded counts approximately 10% of control values, as did uptake in the presence of the dopamine uptake inhibitor, nomifensine maleate (2 μM, Sigma).

Statistical analysis

SigmaStat™ for windows (version 2.0) data analysis software (Jandel Scientific, San Rafael, Calif.) was used for statistical analysis. Results were compared by one-way analysis of variance (ANVOA) followed by a post hoc Bonferroni test for statistical differences between the groups. In experiments where only a single comparison was made, a Student's t-test was used for calculation of statistical significance.

Results

Figure 13:
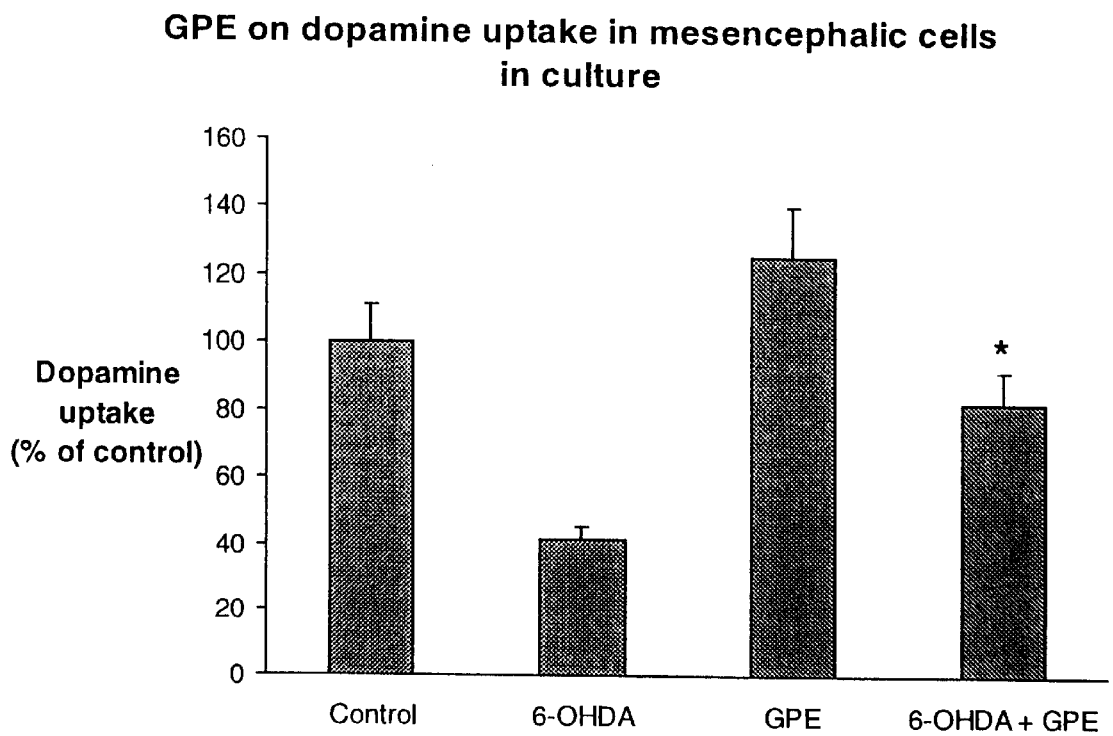
FIG. 13: shows the effect of GPE on dopamine uptake in 6-OHDA treated dopaminergic neurons in vitro.

The results are shown in FIG. 13. As can be seen, GPE protects mesencephalic neurons (which are dopaminergic) from 6-OHDA toxicity in culture.

Summary of Experiments

GPE (In these experiments, dissolved in 0.15M phosphate buffered saline) administered in a single dose given in the period commencing with the time of the CNS injury through to about 8 hours thereafter (and including a time point of about 2 hours after the neural injury has shown therapeutic effect in reducing or eliminating the severity of CNS damage suffered after a neural injury. GPE is especially useful in reducing neuronal loss, infarction, and loss of glial and other cells associated with CNS injury. Thus it can be seen that in at least the preferred forms of the invention a method and/or medicament for treating CNS damage is provided which is able to substantially prevent or treat CNS damage. CNS damage may be associated with asphyxia, hypoxia, toxins, infarction, ischemia or trauma. It will be appreciated that the main application of the invention is to humans. However, the usefulness of the invention is not limited thereto and treatment of other non-human animals, especially mammals is also within the scope of the invention.

The present invention, therefore, recognises the role of an administration of a medicament comprising GPE and/or other compounds of similar effect into a patient at or following a CNS injury with the consequential result that CNS damage is minimised by preventing the otherwise consequential, self-induced damage that would occur following the injury, i.e. it is not involved with the repair of damage that has already occurred but to a treatment at, or subsequent, to the injury but before the consequential long term damage occurs thereby minimising the occurrence of such damage.

EXAMPLE 1

Alleviation of brain damage to an infant or neonatal mammal resulting from perinatal asphyxia Basing the dose rates on our rat and fetal sheep models a suitable method for alleviation of brain damage is to infuse the infant's circulation by intravenous rout with GPE or an analogue thereof in normal saline at a preferred dose rate ip the range 0.1 μg/kg to 10 mg/kg and more preferably about 1 mg/kg from within about 12 h of the onset of fetal distress until about 120 h later. A higher loading dose may be used at the commencement of treatment. Alternatively GPE may initially be administered via the maternal circulation in a higher intravenous dose rate of about 5 mg/kg, while the placenta is largely functional. Alternatively intraventricular infusion at about 10 μm/kg in artificial CSF into the lateral ventricle may be used in indicated.

EXAMPLE 2

Alleviation of brain damage to human or mammal resulting from stroke

Basing the dose rates on our rat and fetal sheep models a suitable method for alleviation of brain damage is to infuse the patients circulation by intravenous route with GPE or an analogue thereof in normal saline at a preferred dose rate in the range of 0.1 μg/kg to 10 mg/kg and more preferably about 1 mg/kg from within about 12 h of the onset of neurological signs until about 120 h later. A higher loading dose may be used at the commencement of treatment. Alternatively the same dose may be administered by close carotid injection. Alternatively intraventricular infusion at about 10 μg/kg in artificial CSF into the lateral ventricle may be used if indicated.

EXAMPLE 3

Alleviation of brain damage to human and mammal resulting from intracerebral haemorrhage.

Basing the dose rates on our rat and fetal sheep models a suitable method for alleviation of brain damage is to infuse the patients circulation intravenous route with GPE or an analogue thereof in normal saline at a preferred dose rate in the range of 0.1 μg/kg to 10 mg/kg and more preferably about 1 mg/kg until about 120 h after the onset on the haemorrhage. A higher loading does may be used at the commencement of treatment. Alternatively intraventricular infusion at about 10 μg/kg in artificial CSF into the lateral ventricle may be used if indicated.

EXAMPLE 4

Alleviation of brain damage to human or mammal resulting from traumatic head injury.

Basing the dose rates on our rat and fetal sheep models a suitable method for alleviation of brain damage is to infuse the infant's circulation by intravenous route with GPE or an analogue thereof in normal saline at a preferred dose rate in the range of 0.1 μg/kg to 10 mg/kg and more preferably about 1 mg/kg from within about 12 h of the injury until about 120 h later. A higher loading dose may be used at the commencement of treatment. Alternatively intraventricular infusion at about 10 μg/kg in artificial CSF into the lateral ventricle may be used if indicated.

EXAMPLE 5

Peripheral administration of GPE is effective.

The objective of this study was to compare the effects of treatment with GPE to that of a vehicle given 2 hours after an hypoxic-ischemic injury. The dose range of 2 to 200 μg was chosen to span a range of systemic doses that are greater than that required centrally (see experiment 3).

Unilateral hypoxic-ischemic injury was induced in 21 day old, 45±5 g Wistar rats. The rats underwent unilateral carotid ligation under light halothane anaesthesia.

Following one hour recovery they were placed in an incubator at 34 deg C. 85±5% humidity for one hour before the injury. They were subjected to 1 min inhalation hypoxia (Fi02.8.0%) and then returned to room temperature (22 deg C.) and normoxia. Two hours after the termination of the injury, a single intraperitoneal injection of 0.25 ml of 2, 20 or 200 µg GPE per rat, or saline alone was given. The animals were then maintained for 120 hrs, anaesthetized and the brains were fixed for histological assessment.

Figure 5:
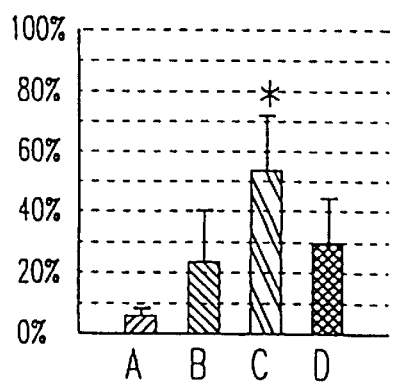
FIG. 5: shows the dose-response effect of GPE on neuronal outcome in the hippocampus (CA1-2 region), after peripheral (intraperitoneal) administration of GPE. The vertical axis shows the R/L ratio; the ratio between the unligated and the ligated sides of the brain.

Surviving and dead neurons were discriminated using the thionin/acid fuchsin staining technique (Guan et al J Cereb Blood Flow Metab. 13:609–616 (1993). The results, in which the height of a point is given by the ratio as a percentage of live neurones in the CA1-2 region on the right side to the number on the left side are shown in FIG. 5. Column A is vehicle, column B is 2 µg of GPE, column C is 20 µg of GPE, and column D is 200 µg of GPE. In this figure, the P value (0.031) was calculated by a method using one way ANOVA comparing many groups after Arcsin transformation.

GPE therapy (20 µg) reduced the loss of neurons in the CA1-2 region of the hippocampus (p<0.05). Thus a single peripheral injection of GPE following an asphyxial injury in the rat was associated with a marked improvement in outcome as assessed histologically.

Options: Our choice of the intraperitoneal route was at least partly dictated by he difficulty of any other routes in such small animals. While it is likely that the intraperitoneal route offers better access of GPE to the circulation and hence to the blood-brain barrier, other routes such as intravenous, intramuscular, or subcutaneous routes also appear to be available although the effective dose rate is likely to be greater.

The above experiment shows that the advantages of GPE over previously favoured IGF-1 treatments include that it (unlike IGF-1) can cross the blood-brain barrier and so can gain access to the CNS from a peripheral site.

Pharmacology

Apart from the dose-response experiments on which FIG. 5 is based, we have not yet studied the pharmacological properties of GPE. We expect it to have a similar half-life in blood to other peptides; we expect that the liver and kidneys will relatively rapidly take up circulating GPE, and we expect that it has a relatively large therapeutic ratio. In view of the expected rapid uptake, intravenous administration is preferably in the form of a steady infusion.

ADVANTAGES

Some advantages offered by this invention, especially over IGF-1 and the like include:

(1) The active ingredients are easy to synthesise either in vitro or by other means such as by recombinant techniques.

(2) The small molecule can diffuse readily through the body and between compartments (e.g. the blood-brain barrier, and mucous membranes), aiding in the choice of methods for its administration and its ability to reach sites where injury has occurred.

We have shown that intraperitoneal administration, to give one non-CSF example, is effective.

(3) The small molecule is unlikely to present a challenge to the immune system, so it may be administered over extended periods and it may be administered prophylactically.

(4) Species differences are unlikely to be important.

In the specific case of dopaminergic neurons, GPE is effective to protect these against death. GPE and its analogues therefore have specific application in treating disorders and diseases which affect dopaminergic neurons, particularly Parkinson's disease.

Although the present invention is defined broadly above, it will be appreciated by those skilled in the art that it is not limited thereto but includes embodiments of which the description provides examples. Finally, it will be appreciated that various alterations and modifications may be made to the foregoing without departing from the scope of this invention as claimed.

What is claimed is:

1. A method for protecting dopaminergic neurons of a mammal against death resulting from Parkinson's disease comprising the step of administering to said mammal a neuroprotective amount of the tripeptide gly-pro-glu (GPE).

2. A method as claimed in claim 1 in which GPE is administered subsequent to onset of Parkinson's disease but prior to death of said dopaminergic neurons.

3. A method as claimed in claim 2 in which GPE is administered in the form of a pharmaceutical composition including a pharmaceutically acceptable carrier therefor.

4. A method as claimed in claim 1 in which GPE is administered directly to where the dopaminergic neurons to be protected are located.

5. A method as claimed in claim 4 wherein GPE is administered directly to the brain or cerebrospinal fluid by cerebro-ventricular injection, by injection into the cerebral parenchyma or through a surgically inserted shunt into the lateral cerebro ventricle of the brain.

6. A method as claimed in claim 5 wherein GPE is administered by cerebro-ventricular injection.

7. A method as claimed in claim 4, wherein GPE is administered in combination with artificial cerebrospinal fluid.

8. A method as claimed in claim 1, wherein GPE is administered systemically for transport to where the dopaminergic neurons to be protected are located.

9. A method as claimed in claim 8, wherein GPE is administered through an intravenous, oral, rectal, nasal, subcutaneous, inhalation, intraperitoneal or intramuscular route.

10. A method as claimed in claim 9 wherein GPE is administered by intraperitoneal injection.

11. A method as claimed in claim 1 wherein the dosage range of GPE administered is from about 1 µg to about 100 mg of GPE per kg of body weight of the mammal.

* * * * *